United States Patent [19]

Edwards et al.

[11] Patent Number: 5,428,018

[45] Date of Patent: Jun. 27, 1995

[54] PHENYLALANINE ANALOGS OF BOMBESIN

[75] Inventors: Judson V. Edwards, Conroe, Tex.; Bradford O. Fanger, Cincinnati, Ohio

[73] Assignee: Merrell Dow Pharmaceuticals Inc., Cincinnati, Ohio

[21] Appl. No.: 263,905

[22] Filed: Jun. 22, 1994

Related U.S. Application Data

[63] Continuation of Ser. No. 833,834, Feb. 7, 1992, abandoned.

[51] Int. Cl.[6] .................... A61K 38/00; C07K 5/00; C07K 7/00; C07K 15/00
[52] U.S. Cl. ........................ 514/15; 514/16; 530/327; 530/328
[58] Field of Search ............ 514/15, 16; 530/328, 530/327

[56] References Cited

U.S. PATENT DOCUMENTS

| | | |
|---|---|---|
| 4,297,346 | 10/1981 | Rips et al. |
| 4,421,744 | 12/1983 | Gormley |
| 4,631,270 | 12/1986 | Yankeelov et al. |
| 4,871,717 | 10/1989 | Coy et al. .................. 514/11 |
| 5,028,692 | 7/1991 | Oliff et al. |
| 5,047,502 | 9/1991 | Oliff et al. |

FOREIGN PATENT DOCUMENTS

| | | |
|---|---|---|
| 313158 | 10/1988 | European Pat. Off. |
| 315367 | 10/1988 | European Pat. Off. |
| 0309297 | 3/1989 | European Pat. Off. ........ C07K 7/00 |
| 0339193 | 11/1989 | European Pat. Off. ........ C07K 7/06 |
| 0345990 | 12/1989 | European Pat. Off. ........ C07K 7/06 |
| 434979 | 11/1990 | European Pat. Off. |
| 0468497 | 1/1992 | European Pat. Off. |
| 8909232 | 10/1989 | WIPO |
| 9001037 | 2/1990 | WIPO |
| 9003980 | 4/1990 | WIPO |
| 9106563 | 5/1991 | WIPO |
| 9117181 | 11/1991 | WIPO |
| 9209626 | 6/1992 | WIPO |

OTHER PUBLICATIONS

Edwards et al., Pept. Chemistry and Biology, Proc., 12th A.P.S., 1992, pp. 52–53.

Kinzie, et al. "Three-Dimensional Modeling and Site-Directed Mutagenesis of the Bombesin/GRP Receptor Ligand-Binding Site," American Federation for Clinical Research, Carmel, Calif., Feb. 5–8, 1992.

Edwards, "Amide bond substitutions and conformational contraints applied to bombesin antagonists," Peptides, Chemistry and Biology, Proc. 12th A.P.S., Jun. 16–21, 1991, Escom, Leiden 1992.

Coy, et al., "Short-chain bombesin receptor antagonists with IC50S for cellular secretion and growth appraoching the picomolar region", Peptides Chemistry and Biology, Proc. 11th A.P.S., Jul. 9–14, 1989, Escom Leiden 1990.

Coy, et al., "Receptors for mammalian bombesin/GRP and neuromedin B have greatly differing ligand binding requirements", Peptides, Chemistry and Biology, Proc. 12th A.P.S., Jun. 16–21, 1991, Escom, Leiden 1992.

Wang, et al., J. of Biological Chemistry, vol. 265(26):15695–15703, (Sep. 15, 1990).

(List continued on next page.)

Primary Examiner—Jill Warden
Assistant Examiner—A. M. Davenport
Attorney, Agent, or Firm—Kenneth J. Collier

[57] ABSTRACT

Disclosed are Agonists and Antagonists of bombesin which are derivatives of naturally occurring bombesin possessing modified derivatives of phenylalanine. Agonist and antagonist activities are confirmed using conventional competitive binding and biochemical assays as well as conventional physiological tests and the use of these derivatives in a variety of conditions.

Use of these peptides may be useful for stimulating or antagonising growth of tissues, especially lung, and of digestion. Treatment comprises administering to a patient in need thereof, an effective amount of a bombesin analog.

8 Claims, No Drawings

OTHER PUBLICATIONS

Coy, David, H., et al., J. Biol. Chem., 263(11), 5056–5060 (1989).
Mahmoud, S., et al., Life Sciences, 44(5), 367–373 (1989).
Rossowski, W. J., et al., Scand. J. Gastroenterol., 24(1), 121–128 (1989).
Bologona, Mauro, et al., Cancer, 63, 1714–1720 (1989).
Jensen, R. T., et al., Nature, 309, 61–63 (1984).
Coy, David H., et al., J. Biol. Chem., 264(25), 14691–14697 (1989).
Cowan, Alan, TIPPS, 101, 1–3 (1988).
Heimbrook, David C., et al., J. Biol. Chem. 264(19), 11258–11262 (1989).
Mukai, Hidehito, et al., Am. Physiol. Soc., E235(1989).
Heimbrook, David D., UCLA Symp., Mol. Cel. Biol., 86, 295–307 (1989).
Saeed, Z. A., Peptides, 10, 597–603 (1989).
Woll, Pennnela, J. et al., Proc. Natl. Acad. Sci. USA, 85, 1859–1863 (1988).
Zhang, Li, et al., BBA 972, 37–44 (1988).
Woll, Pennela, J. et al., Growth Factors, 1, 75–83 (1988).
Bepler, Gerold, et al., Peptides, 9, 1367–1372 (1989).
Edwards, J. V., et al., 1992 Gordon Conference-Pep-
Merali, Zul, et al., Synapse, 2, 282–287 (1988).
Dutta, Anand S., et al., J. Med. Chem. 29, 1171–78 (1986).
Marki, et al., Peptides, 2(2) 169–177 (1981).
Lebacq-Verheyden, A. M., et al., Bombesin and Gastrin Releasing Peptide: Neuropeptides Secretogogues, and Growth Factors, Chapter 21, In Peptide Growth Factors and Their Receptors II, editors Sporn, M., and Roberts, A. B., Springer-Verlag, NY (1990).
Erspamer, G. F., et al, Regulatory Peptides, 21, 1–11 (1988).
Edwards, J. V., et al, 1990 Gordon Conference on the Chemistry and Biology of Peptides, Feb. 5–9, 1990 Ventura, Calif.
Antony, V. B., et al., Clin. Res. 37, 145A (1989).
Woll, P. J., et al., BBRC, 155(1), Aug., 359–365 (1988).
Spatola, A. F., et al., Chem. Abs. 111(11), abst. no. 90576e (1989).
Smith, C. W., et al., Chem Abs. 109(3), abst. no. 23372f, 662 (1988).
Edwards, J. V., et al., BBRC 136(2), 703–6 (1986).
Edwards, J. V., et al., Int. J. Peptide Protein Res. 28, 603–612 (1986).
tides, Chemistry and Biology, Ventura, Calif., Feb. 9–14, 1992.

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: protein ( i x ) FEATURE:
        ( A ) NAME/KEY: Modified-site
        ( B ) LOCATION: 27
        ( D ) OTHER INFORMATION: /note="Amidation of methionine at carboxy end"

( i x ) FEATURE:
        ( A ) NAME/KEY: Modified-site
        ( B ) LOCATION: 1..27
        ( D ) OTHER INFORMATION: /note="Human gastric releasing
              peptide (human GRP)"

( x i ) SEQUENCE DESCRIPTION: SEQ ID NO:1:

Val  Pro  Leu  Pro  Ala  Gly  Gly  Gly  Thr  Val  Leu  Thr  Lys  Met  Tyr  Pro
1                   5                        10                         15

Arg  Gly  Asn  His  Trp  Ala  Val  Gly  His  Leu  Xaa
              20                       25

( 2 ) INFORMATION FOR SEQ ID NO:2:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: protein ( i x ) FEATURE:
        ( A ) NAME/KEY: Modified-site
        ( B ) LOCATION: 1
        ( D ) OTHER INFORMATION: /note="Xaa ispyrrolidone
              carboxylic acid"

( i x ) FEATURE:
        ( A ) NAME/KEY: Modified-site
        ( B ) LOCATION: 14
        ( D ) OTHER INFORMATION: /note="Amidation of methionine at
              carboxy end"

( i x ) FEATURE:
        ( A ) NAME/KEY: Modified-site
        ( B ) LOCATION: 1..14
        ( D ) OTHER INFORMATION: /note="Amphibian bombesin"

( x i ) SEQUENCE DESCRIPTION: SEQ ID NO:2:

Xaa  Gln  Arg  Leu  Gly  Asn  Gln  Trp  Ala  Val  Gly  His  Leu  Xaa
1                   5                        10

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Xaa is pyrrolidone
              carboxylic acid"

( i x ) FEATURE:
        ( A ) NAME/KEY: Modified-site
        ( B ) LOCATION: 9
        ( D ) OTHER INFORMATION: /note="Amidation of methionine at
              carboxy end"

( i x ) FEATURE:
        ( A ) NAME/KEY: Modified-site
        ( B ) LOCATION: 1..9
        ( D ) OTHER INFORMATION: /note="Amphibian litorin"

( x i ) SEQUENCE DESCRIPTION: SEQ ID NO:3:

Xaa  Gln  Trp  Ala  Val  Gly  His  Phe  Xaa
1                   5

( 2 ) INFORMATION FOR SEQ ID NO:4:

( i ) SEQUENCE CHARACTERISTICS:

(A) LENGTH: 9 amino acids
        (B) TYPE: amino acid
        (D) TOPOLOGY: linear (i i) MOLECULE TYPE: peptide (i x) FEATURE:
        (A) NAME/KEY: Modified-site
        (B) LOCATION: 1
        (D) OTHER INFORMATION: /note="Ac-D-Phe"

(i x) FEATURE:
        (A) NAME/KEY: Modified-site
        (B) LOCATION: 9
        (D) OTHER INFORMATION: /note="Delta z-Phe-OMe"

(x i) SEQUENCE DESCRIPTION: SEQ ID NO:4:

Xaa  Gln  Trp  Ala  Val  Gly  His  Leu  Xaa
    1                   5

(2) INFORMATION FOR SEQ ID NO:5:

(i) SEQUENCE CHARACTERISTICS:
        (A) LENGTH: 9 amino acids
        (B) TYPE: amino acid
        (D) TOPOLOGY: linear (i i) MOLECULE TYPE: peptide (i x) FEATURE:
        (A) NAME/KEY: Peptide
        (B) LOCATION: 1
        (D) OTHER INFORMATION: /note="Ac-D-Phe"

(i x) FEATURE:
        (A) NAME/KEY: Modified-site
        (B) LOCATION: 9
        (D) OTHER INFORMATION: /note="N(Me), delta z-Phe-OMe"

(x i) SEQUENCE DESCRIPTION: SEQ ID NO:5:

Xaa  Gln  Trp  Ala  Val  Gly  His  Leu  Xaa
    1                   5

(2) INFORMATION FOR SEQ ID NO:6:

(i) SEQUENCE CHARACTERISTICS:
        (A) LENGTH: 9 amino acids
        (B) TYPE: amino acid
        (D) TOPOLOGY: linear (i i) MOLECULE TYPE: peptide (i x) FEATURE:
        (A) NAME/KEY: Modified-site
        (B) LOCATION: 1
        (D) OTHER INFORMATION: /note="Ac-D-Phe"

(i x) FEATURE:
        (A) NAME/KEY: Modified-site
        (B) LOCATION: 9
        (D) OTHER INFORMATION: /note="N(Et), delta z-Phe-OMe"

(x i) SEQUENCE DESCRIPTION: SEQ ID NO:6:

Xaa  Gln  Trp  Ala  Val  Gly  His  Leu  Xaa
    1                   5

(2) INFORMATION FOR SEQ ID NO:7:

(i) SEQUENCE CHARACTERISTICS:
        (A) LENGTH: 9 amino acids
        (B) TYPE: amino acid
        (D) TOPOLOGY: linear (i i) MOLECULE TYPE: peptide (i x) FEATURE:

(A) NAME/KEY: Modified-site
(B) LOCATION: 1
(D) OTHER INFORMATION: /note="Ac-D-Phe"

(ix) FEATURE:
(A) NAME/KEY: Modified-site
(B) LOCATION: 9
(D) OTHER INFORMATION: /note="Delta E-Phe-OMe"

(xi) SEQUENCE DESCRIPTION: SEQ ID NO:7:

Xaa Gln Trp Ala Val Gly His Leu Xaa
1               5

(2) INFORMATION FOR SEQ ID NO:8:

(i) SEQUENCE CHARACTERISTICS:
(A) LENGTH: 9 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /note="Ac-D-Phe"

(ix) FEATURE:
(A) NAME/KEY: Modified-site
(B) LOCATION: 6
(D) OTHER INFORMATION: /note="D-Ala"

(ix) FEATURE:
(A) NAME/KEY: Modified-site
(B) LOCATION: 9
(D) OTHER INFORMATION: /note="N(Me), delta z-Phe-OMe"

(xi) SEQUENCE DESCRIPTION: SEQ ID NO:8:

Xaa Gln Trp Ala Val Xaa His Leu Xaa
1               5

(2) INFORMATION FOR SEQ ID NO:9:

(i) SEQUENCE CHARACTERISTICS:
(A) LENGTH: 9 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /note="Glp"

(ix) FEATURE:
(A) NAME/KEY: Modified-site
(B) LOCATION: 7
(D) OTHER INFORMATION: /note="Delta z-Phe"

(xi) SEQUENCE DESCRIPTION: SEQ ID NO:9:

Xaa Gln Trp Ala Val Gly Xaa Phe Leu
1               5

(2) INFORMATION FOR SEQ ID NO:10:

(i) SEQUENCE CHARACTERISTICS:
(A) LENGTH: 9 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1

(D) OTHER INFORMATION: /note="Glp"

(ix) FEATURE:
    (A) NAME/KEY: Modified-site
    (B) LOCATION: 9
    (D) OTHER INFORMATION: /note="Delta z-Phe-OMe"

(xi) SEQUENCE DESCRIPTION: SEQ ID NO:10:

```
Xaa Gln Trp Ala Val Gly His Leu Xaa
1               5
```

(2) INFORMATION FOR SEQ ID NO:11:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note="Glp"

(ix) FEATURE:
        (A) NAME/KEY: Modified-site
        (B) LOCATION: 9
        (D) OTHER INFORMATION: /note="N(CH3)delta z-Phe-OMe"

(xi) SEQUENCE DESCRIPTION: SEQ ID NO:11:

```
Xaa Gln Trp Ala Val Gly His Leu Xaa
1               5
```

(2) INFORMATION FOR SEQ ID NO:12:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:12:

```
Xaa Gly Gln Thr Ala Val Gly His Leu
1               5
```

PHENYLALANINE ANALOGS OF BOMBESIN

Cross-Reference to Related Application

This is a continuation of application Ser. No. 07/833,834, filed Feb. 7, 1992, which is herein incorporated by reference and now abandoned.

FIELD OF THE INVENTION

This invention relates to novel phenylalanine analogs of Bombesin which are potentially useful as pharmaceuticals.

BACKGROUND OF INVENTION

Bombesin (ID#2) is a 14 amino acid peptide, originally isolated from the skin of the frog Bombina bombina. Bombesin is also structurally related to a number of other peptides including Gastrin Releasing Peptide (ID#1), and Litorin (ID#3) (See Sequence Identification).

Bombesin is known to have a range of effects including stimulation of the nervous system, reduction of renal blood flow, secretion of pituitary hormones, growth promotion, memory retention, induction of myoelectric and contractile activity of intestinal myocytes, induction of gastric and pancreatic secretion, and bolster the immune system. There has been considerable interest in modulating these activities in the design and development of bombesin analogs as possible mimics or inhibitors of bombesin action in the body.

The bombesin-dependent responses occur through a class of high-affinity ($KD=1$ nm) cell surface receptors that bind bombesin. Binding of bombesin to its cell surface receptor elicits cell mitogenic responses in a number of tissues. The mitogenic response has been demonstrated in a number of cell types including Swiss 3T3 embryo fibroblast cells, human bronchial epithelial cells, human small cell lung carcinoma cells, rat gastrin cells, and rat pancreatic cells. Similarly, bombesin induction of gastric and pancreatic secretions, important for digestive functions, occur through the receptors found on cells of pancreatic (B-Cells) and intestinal gastrin cells (G-cells).

Binding of bombesin to its extracellular receptor evokes a number of intracellular signals including activation of G-proteins, which in turn activates phospholipase C (PLC). PLC in turn converts phosphatidylinositol phosphate (PI) into inositol 1,4,5,-triphosphate ($IP_3$) and diacylglycerol (DAG). $IP_3$ and DAG are believed to be intracellular signals for cellular mediated events.

Structure-activity studies indicate that receptor-binding generally requires a peptide ligand containing an amidated C-terminus, and generally the presence of the last eight amino acids. Recent work has concentrated on modifying the carboxy terminal (C-terminal) region of bombesin to selectively modulate the receptor interaction utilizing a variety of different types of C-terminal modified analogs. These modifications have included, for example, incorporation of D-amino acids, non-peptide bonds, amide, and ester modifications. These alterations have given rise to certain peptides having improved characteristics.

The applicants have prepared linear peptide analogs of the natural bombesin containing dehydrophenylalanine. The applicants have demonstrated that these analogs act at the bombesin receptor and elicit or prevent required intracellular signals for cellular response of bombesin. The peptide analogs of this invention potentially possess significant antimitotic and/or anti-secretory activity and therefore may allow for a scientifically interesting and therapeutically significant adjunct to growth therapy and/or the treatment of digestive disorders. Moreover, the presence of the modified phenylalanine functionalities may provide for enhanced potency and extended duration of action.

SUMMARY OF THE INVENTION

Claimed are peptide derivatives of the formula 1 and 2 given below:
Peptides of formula 1 are of the structure
Glp-Gln-Trp-Ala-Val-Gly-A1-Phe*-A2-Y ( formula 1 )
wherein;

$A_1$ is His, Leu, His-Leu, or a bond;

Phe* is a modified phenylalanine derivate selected from the group consisting of phe, $\Delta^z$Phe, and $\Delta^E$Phe wherein said modified phenylalanine derivatives may be further substituted by a $C_1$–$C_4$ alkyl group at the alpha nitrogen of said modified phenylalanine derivative;

$A_2$ is Phe, Leu, Phe-Leu, or a bond; and

Y is a carboxy terminal substituent selected from OH, ($C_1$–$C_8$) alkoxyester, carboxamide, mono or di ($C_1$–$C_8$) alkyl amide, mono or di ($C_1$–$C_8$) alkylamine, ($C_1$–$C_4$) thioalkylether; or said compounds of formula 1 are pharmaceutically acceptable salt thereof.

Peptides of formula 2 are of the structure
X-A3-Phe*-A4-Gln-Trp-Ala-Val-Gly-His-Leu-Y (formula 2)
wherein;

$A_3$ is Glp, or a bond;

Phe* is a modified phenylalanine derivate selected from the group consisting of phe, $\Delta^z$Phe, and $\Delta^E$Phe wherein said modified phenylalanine derivatives may be further substituted by a $C_1$–$C_4$ alkyl group at the alpha nitrogen of said modified phenylalanine derivative;

$A_4$ is Gly or a bond;

X is an amino terminal substituent selected from hydrogen, one or two alkyl groups from 1 to 8 carbon atoms, one or two acyl groups of from 2 to 8 carbon atoms, carbobenzyloxy or t-butyloxy carbonyl; unless the amino terminal acid is Glp and thereby X is omitted;

Y is a carboxy terminal substituent selected from OH, ($C_1$–$C_8$) alkoxyester, carboxamide, mono or di ($C_1$–$C_8$) alkyl amide, mono or di ($C_1$–$C_8$) alkylamine, ($C_1$–$C_4$) thioalkylether; or said compounds of formula 1 are pharmaceutically acceptable salt thereof.

It is understood that preferred derivatives of formula I and II are contained within the groupings and maybe elected to form subgroupings containing those elected substituents to be preferred derivatives of formula I and II.

DETAILED DESCRIPTION OF THE INVENTION

The following common abbreviations of; (1) amino acids and their three letter codes, (2) modified phenylalanines and their structures, and (3) terminal amino and carboxy substituents used throughout this specification:

| (1): THE AMINO ACIDS AND THEIR THREE LETTER CODE | |
|---|---|
| L-AMINO ACIDS | D-AMINO ACIDS |

-continued

| | |
|---|---|
| Ala - alanine | ala - D-alanine |
| Arg - arginine | arg - D-arginine |
| Asn - asparagine | asn - D-asparagine |
| Asp - aspartic acid | asp - D-aspartic acid |
| Cys - cysteine | cys - D-cysteine |
| Gly - glycine | |
| Glu - glutamic acid | glu - D-glutamic acid |
| Val - valine | val - D-valine |
| Gln - glutamine | gln - D-glutamine |
| His - histidine | his - D-histidine |
| Ile - isoleucine | ile - D-isoleucine |
| Leu - leucine | leu - D-leucine |
| Lys - lysine | lys - D-lysine |
| Phe - phenylalanine | phe - D-phenylalanine |
| Met - methionine | met - D-methionine |
| Pro - proline | pro - D-proline |
| Ser - serine | ser - D-serine |
| Thr - threonine | thr - D-threonine |
| Trp - tryptophan | trp - D-tryptophan |
| Tyr - tyrosine | tyr - D-tyrosine |

(2): MODIFIED PHENYLALANINES AND THEIR STRUCTURES

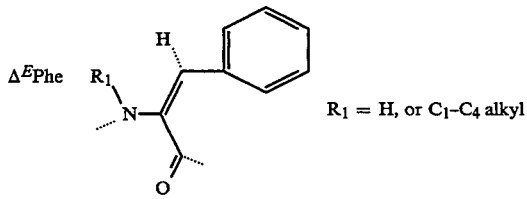

$\Delta^E$Phe  $R_1 =$ H, or $C_1$–$C_4$ alkyl

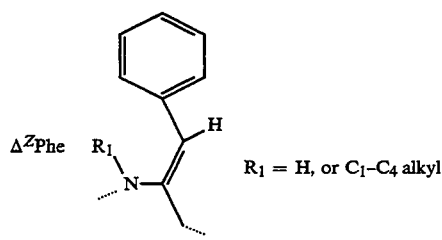

$\Delta^Z$Phe  $R_1 =$ H, or $C_1$–$C_4$ alkyl (3): AMINO AND CARBOXY TERMINAL ACID SUBSTITUENTS Ac - acetyl
Azt - azetidine-2-carboxylate
Cin - cinnamoyl
DhCin - 3,4-dihydrocinnamoyl
Glt - glutaryl
Mal - maleyl
Oac - 8-aminooctanoic acid
Oct - n-octane
Suc - succinyl
Glt - glutaryl
Tfa - trifluoroacetyl
- C-terminal amide

BOMBESIN PEPTIDES

As many as 13 bombesin-like peptides have been isolated from amphibian sources, one from avian proventriculus, and 5 or 6 from mammalian tissues. The bombesin peptides may be divided into 3 subfamilies on the basis of their primary structure, their pharmacological activity, and their receptor affinity. The bombesin subfamily is characterized by the C-terminal tetrapeptide -Gly-His-Leu-Met-NH$_2$, the litorin/ranatensin subfamily by the tetrapeptide -Gly-His-Phe-Met-NH$_2$, and the phyllolitorin subfamily by the tetrapeptide -Gly-Ser-Phe(Leu)-Met-NH$_2$.

Present within the bombesin subfamily are the gastrin-releasing peptides (GRPs) of mammalian origin. Human, porcine, and canine GRPs differ from each other in the N-terminal dodecapeptide, but have an identical carboxy amino acid sequences (residues 13–27). Moreover, the C-terminal decapeptide of the mammalian GRPs is identical to the C-terminal decapeptide of frog bombesin, with only the difference of having a His residue substituted for the Gln residue at position 8 from the C-terminus. A mammalian peptide present within the litorin/ranatensin-like family is neuromedin B.

A Sequence Identification of some of the sequence variations of bombesin is included prior to the claims: e.g. Bombesin (ID#2), Gastrin Releasing Peptide (ID#1), Litorin (ID#3).

Herein, the term "bombesin or natural variant thereof" includes all subfamilies and natural variants of bombesin [See Falconieri, et. al. Regulatory Peptides, 21, 1–11, 3, (1988), for a listing of known Bombesin related peptides and is incorporated herein by reference] including sequences related to GRP, and litorin and the like. The term "variations thereof" for substituents $A_1$, $A_2$, $A_3$, $A_4$, as defined optionally includes 1–5 amino acids of bombesin or related variants contiguous with a consecutive region of internal amino acids unless it is a bond or unless the amino or carboxy terminal acid is a cyclic derivative and thereby the sequence of 1–5 amino acids is omitted.

Amino Acids & Modifications

Herein, as is customary, the structure of peptides when written is such that the amino terminal end appears on the left side of the page and the carboxy terminal end appears on the right side of the page.

An alkyl group of 1–8 carbon atoms and the alkyl portion of an alkoxy group is taken to include straight, branched, or cyclic alkyl groups, for example, methyl, ethyl, propyl, isopropyl, butyl, isobutyl, tert-butyl, pentyl, isopentyl, sec-pentyl, cyclopentyl, hexyl, isohexyl, cyclohexyl and cyclopentylmethyl, heptyl, octyl(Oct), and 8-aminooctanoic acid(Aoc). An acyl group of from 2 to 8 carbon atoms is taken to include straight, branched, cyclic, and saturated and unsaturated acyl groups having 1 or 2 carbonyl moieties per group, for example, acetyl(Ac), azetidine-2-carboxylate(Azt), benzoyl, succinyl, cinnamoyl(Cin), 3,4-dihydrocinnamoyl(DhCin), maleyl(Mal), palmityl, lauryl, octanoyl, and glutaryl(Glt). Both alkyl and acyl substituents are taken to include those groups with halogen substituents, where a halogen group is a fluoro, chloro, bromo, or iodo, for example, trifluoroacetyl(Tfa). Cyclic derivatives of N-terminal amino acid residues include pyroglutamic acid (pGlu) and homoserine lactone (Hse).

An alkyl group of 1–4 carbon atoms and the alkyl portion of an alkoxy group is taken to include straight and branched alkyl groups, for example, methyl, ethyl, propyl, isopropyl, butyl, isobutyl, tert-butyl, The naturally occurring amino acids, with the exception of glycine, contain a chiral carbon atom. Unless otherwise specifically indicated, the optically active amino acids, referred to herein, are of the L-configuration (See Amino Acids and Their Letter Codes found herein). However, any of the amino acids of the $A_1$, $A_2$, $A_3$, $A_4$ group can be specifically designated to be either the of the D- or L-configuration. The amino acids of $A_1$–$A_4$ may be further designated to consist of the naturally occurring amino acids which are glycine, alanine, valine, leucine, isoleucite, serine, methionine, threonine, phenylalanine, tyrosine, tryptophan, cysteine, proline, histidine, aspartic acid, asparagine, glutamic acid, glutamine, arginine, ornithine, and lysine. Also included would be the D-isomers of the naturally occurring amino acids; D-alanine, D-valine, D-leucine, D-isoleucine, D-serine, D-methionine, D-threonine, D-phenylalanine, D-tyrosine, D-tryptophan, D-cysteine, D-proline, D-histidine, D-aspartic acid, D-asparagine, D-glutamic acid, D-glutamine, and D-arginine. As indicated earlier, D amino acids may be represented by the first letter of their 3 letter or 1 letter code being a lower case letter; i.e for D-Alanine (D-Ala, ala, or a); D-Phenylalanine (D-Phe, phe, or f).

Groups of amino acids can be defined by certain charge characteristics. There are two general characteristics of side chains: nonpolar and polar. The nonpolar residues are made up of these groups: the hydrophobic residues which include those with (1) aliphatic hydrocarbon side chains: Gly, Ala, Val, Leu, Ile, Nle, and Pro; (2) the aromatic group Phe and Trp, and (3) the pseudohydrocarbon, Met. The polar amino acids are made up three groups: (1) the acidic hydrophobic residues Asp, Glu, and Tyr; (2) the neutral residues with the hydroxyl-containing residues, Ser and Thr; the amides, Asn and Gln; the aromatics, Tyr and Trp; the sulfhydryl, Cys, and small structurally accommodating amino acids Ala and Gly; and (3) basic hydrophobic residues His, Lys, and Arg.

Y designates the chemical group(s) that may be utilized to substitute or modify the terminal amino acid unless the terminal substituent is given a cyclized group or of formula 2, the Y is omitted. Further, a given Y substituent is understood to be bonded through the carbonyl of the amino acid (CO—Y). Therefore, Y may be a carboxy terminal acid (—OH), $C_1$–$C_8$ alkoxyester, carboxamide, mono or di $C_1$–$C_8$ alkylester, $C_1$–$C_8$ alkylamine, or $C_1$–$C_4$ thioalkylether, or a pharmaceutically acceptable salt in addition or in conjunction with any of the substituents.

The polypeptides of formula 1 can form pharmaceutically acceptable salts with any nontoxic, organic or inorganic acid. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono, di, and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, and sulfonic acids such as methane sulfonic acid and 2-hydroxyethane sulfonic acid. Salts of the carboxy terminal amino acid moiety include the nontoxic carboxylic acid salts formed with any suitable inorganic or organic bases. Illustratively, these salts include those of alkali metals, as for example, sodium and potassium; alkaline earth metals, such as calcium and magnesium; light metals of Group IIIA including aluminum; and organic primary, secondary, and tertiary amines, as for example, trialkylamines, including triethylamine,, procaine, dibenzylamine, 1-ethenamine, N,N'-dibenzylethylenediamine, dihydroabietylamine, N-(lower)alkylpiperidine, and any other suitable amine.

General Synthesis of Peptides

The peptides of formula 1 of this invention can be prepared by a variety of procedures readily known to those skilled in the art. Such procedures include the solid phase sequential and block synthesis, gene cloning, and combinations of these techniques. The solid phase sequential procedure can be performed using a combination of established solution phase and automated methods known in the art.

Peptides of formula 1 having an amide functionality, wherein Y is an amino substituent, traditionally have the carboxy terminal amino acid attached to a methylbenzhydrylamine type resin. Preparation of peptides with an amide functionality is known to those skilled in the art.

As is known in the art of solid phase peptide synthesis, many of the amino acids bear functionalities requiring protection during synthesis. The use and selection of the appropriate protecting group will depend upon the amino acid to be protected and the presence of other protected amino acid residues on the peptide. Generally, the selection of such a side chain protecting group requires that it must be one which is not removed by cleavage during cleavage of the protecting group of the α-amino moiety. For example, suitable side chain protecting groups for lysine are benzyloxycarbonyl and substituted benzyloxycarbonyl, said substituent being selected from halo (e.g., chloro, bromo, fluoro) and nitro (e.g., 2-clorobenzyloxycarbonyl, p-nitrobenzyloxy-carbonyl, 3,4-dichlorobenzyloxycarbonyl), tosyl, t-amyloxycarbonyl, t-butyloxycarbonyl, and diisopropylmethoxycarbonyl. The alcoholic hydroxyl group of threonine and serine can be protected with an acetyl, benzoyl, tert-butyl, trityl, benzyl, 2,6-dichlorobenzyl, or benzyloxycarbonyl group. The preferred protecting group is benzyl. The selection and use of appropriate protecting groups for each peptide is within the ability of those skilled in the art.

The α-amino protecting group employed with each amino acid introduced into the polypeptide sequence may be any such protecting group known to the art. Among the classes of α-amino protecting groups contemplated are (1) acyl type protecting groups such as: formyl, trifluoroacetyl, phthalyl, toluenesulfonyl (tosyl), benzenesulfonyl, nitrophenylsulfenyl, tritylsulfenyl, o-nitrophenoxyacetyl, and α-chlorobutyryl; (2) aromatic urethane type protecting groups such as benzyloxycarbonyl and substituted benzyloxycarbonyl, such as p-chlorobenzyloxycarbonyl, p-nitrobenzylcarbonyl, p-bromobenzyloxycarbonyl, p-methoxybenzyloxycarbonyl, 1-(p-biphenylyl)-1-methylethoxycarbonyl, α-dimethyl-3,5-dimethoxybenzyloxycarbonyl, and benzhydryloxycarbonyl; (3) aliphatic urethane protecting groups such as tert-butyloxy-carbonyl (Boc), diisopropylmethoxycarbonyl, isopropyloxycarbonyl, ethoxycarbonyl, and allyloxycarbonyl; (4) cycloalkyl urethane type protecting groups such as cyclopentyloxycarbonyl, adamantyloxycarbonyl, and cyclohexyloxycarbonyl; (5) thiourethane type protecting groups such as phenylthiocarbonyl; (6) alkyl type protecting groups such as triphenylmethyl (trityl) and benzyl; and (7) trialkylsilane groups such as trimethylsilane. The preferred a-amino protecting group is tert-butyloxycarbonyl (Boc).

The extension of the peptide sequence was done using standard methodology and that of the manufacturer and that known by people skilled in the art. Extension of the peptide chain, by coupling activated amino acids, is known for both L and D isomers of amino acids and is generally accomplished with coupling agents known to those skilled in the art.

The selection of an appropriate coupling reagent is within the skill of the art. A particularly suitable coupling reagent where the amino acid to be added is Gln, Asn or Arg is N,N'-diisopropylcarbodiimide and 1-hydroxybenzotriazole. The use of these reagents prevents nitrile and lactam formation. Other coupling agents are (1) carbodiimides (e.g., N,N'-dicyclohexylcarbodiimide and N-ethyl-N'-(γ-dimethylaminopropyl-carbodiimide); (2) cyanamides (e.g., N,N-dibenzyl-cyanamide); (3) ketenimines; (4) isoxazolium salts (e.g., N-ethyl-5-phenyl-isoxazolium-3'-sulfonate; (5) monocyclic nitrogen containing heterocyclic amides of aromatic character containing one through four nitrogens in the ring such as imidazolides, pyrazolides, and 1,2,4-triazolides. Specific heterocyclic amides that are useful include N,N'-carbonyldiimidazole and N,N-carbonyl-di-1,2,4-triazole; (6) alkoxylated acetylene (e.g., ethoxyacetylene); (7) reagents which form a mixed anhydride with the carboxyl moiety of the amino acid (e.g., ethylchloroformate and isobutylchloroformate) or the symmetrical anhydride of the amino acid to be coupled (e.g., Boc-Ala-O-Ala-Boc), (8) nitrogen containing heterocyclic compounds having a hydroxy group on one ring nitrogen (e.g., N-hydroxyphthalimide, N-hydroxysuccinimide, and 1-hydroxybenzotriazole), and (9) diphenyl phosphorylazide. Other activating reagents and their use in peptide coupling are described by Kapoor, *J. Pharm. Sci.*, 59, pp. 1-27 (1970). Applicants prefer the use of the symmetrical anhydride as a coupling reagent for all amino acids except Arg, Asn, and Gln.

Each protected amino acid or amino acid sequence is introduced into the solid phase reactor in about a four-fold excess and the coupling is carried out in a medium of dimethylformamide: methylene chloride (1:1) or in dimethylformamide alone, or preferably methylene chloride alone. In cases where incomplete coupling occurs, the coupling procedure is repeated before removal of the α-amino protecting group, prior to the coupling of the next amino acid in the solid phase reactor. The success of the coupling reaction at each stage of the synthesis is monitored by the ninhydrin reaction as described by E. Kaiser et al, *Analyt. Biochem.* 34, 595 (1970).

After completion of coupling of the sequence either the Boc protecting group was left in place or it was removed and the N-terminal amino group alkylated or acylated using those methods known in the art. After the desired N-terminus is formed then displacement of the protecting groups and removal of the peptide from the resin is accomplished using a hydrogen fluoride solution, as known in the art.

An important aspect of the present invention is the incorporation of analogs of phenylalanine into the structure of formula I. Generally the phenylalanine analogs (Phe*) are incorporated into the peptide chain as (1) protected phenylalanine analogs Phe*. Phe* is used generically to refer to those groups and subgroups containing a modified phenylalanine include (1) $A_1$-Phe* and $A_3$-Phe* dipeptide analogs, (2) Phe*-$A_2$ and Phe*-$A_4$ dipeptide analogs, or (3) $A_1$-Phe*-$A_2$ tripeptide analogs. Methods for synthesizing these compounds is disclosed below in Reaction Scheme I.

Synthesis of Protected Phe* Analogs ($R_1$=H)

Compounds of formula I may incorporate subunits of formula I in the sequence having modified phenylalanine analogs (Phe*): (1) $A_1$-Phe* or $A_3$-Phe* dipeptide analogs (collectively herein A-Phe*) (2) Phe*-$A_2$ or Phe*-$A_4$ dipeptide analogs (collectively herein A-Phe*-A), or (3) $A_1$-Phe*-$A_2$ or $A_3$-Phe*-$A_4$ tripeptide analogs (collectively herein A-Phe*-A) according to reaction scheme I, wherein R1 is selected to be hydrogen.

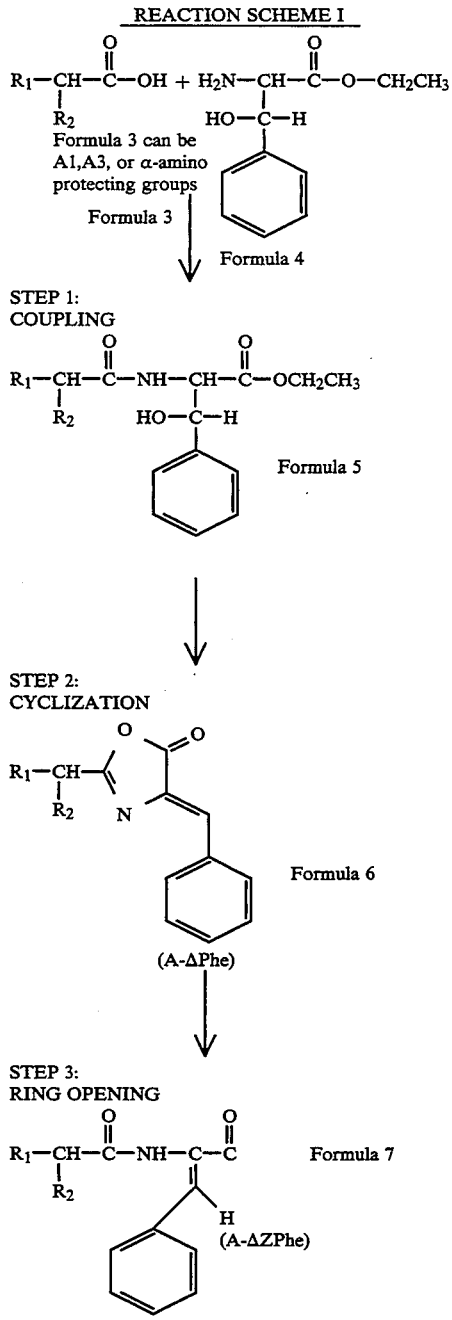

Compounds of formula 3 may either be a defined $A_1$ or $A_3$ amino acid, wherein the amino acid contains the required protecting groups, for synthesis of the subunit structure A-Phe*. If compounds of formula 3 represents a protected amino acid, $R_1$ and $R_2$ are such to form a suitably protected $A_1$ or $A_3$ amino acid for synthesis. Alternatively, compounds of formula 3 can be a suitable α-amino protecting group for the compounds of formula 4 to form subunits of the structure Phe*. Consistent with subunits of Phe* are compounds wherein $A_3$ is a bond to an amino terminal protecting group X, wherein $R_1$ and $R_2$ group are such to form a suitably defined protecting group. If the formula 3 compound is an amino protecting group, such α-carbonyl subtituents include appropriate protected amino acid as the t-butyloxycaronyl-amino acids, or α-amino protecting groups acetyl, propyl, or the like.

A prefered ester of formula 4 is the D,L-3-phenylserine (D,L-βPhSer)ethyl ester as shown, but may be preformed with other suitably acid protecting groups. Similarly, as a preferred embodiment, D,L-Phe may be the salt of the amide (not shown). A preferred salt is the p-toluenesulfonate of the D,L-3-phenylserine alkyl ester.

The first step in the reaction scheme I is to couple compounds of formula 3 and formula 4. Amide bond formation between the compounds of formula 3 and 4 may be made using a number of suitable coupling reagents known in the art to form the compounds of formula 5. One such coupling agent is isobutyl chloroformate.

The second step in the reaction sequence is the cyclization of compound of formula 5. Azalactonization of A-DL-βPhSer is afforded using the Bergmann method. A suitable employment of the Bergmann procedure employs concomitant dehydration of the azylactonized phenylserine residue of formula 5. Upon cyclization through azlactonization the dehydroamino acid containing a double bond is introduced stereoselectively to the $\Delta^Z$ configuration.

The third step in the reaction is ring opening of the azalactone. This is accomplished by nucleophilic attack of the cyclized carbonyl of the ring. Here this strategy can be employed to provide a suitable carboxy terminal protected dedrophenylalalanine (Δphe) or can be employed to form amide bonds to one or more adjoining amino acids, wherein the a-amino group of the subsequent amino acid provides a suitable nucleophile for ring opening of the azalactone. This later strategy can be used to synthesize compounds of Phe*-A subunits A-Phe*-A tripeptide subunits for incorporation into the given peptide sequence.

The fourth step is isolation of phe* peptides having a modified phenylalanine selected in the $\Delta^z$ configuration. Following isolation of the desired phe* configured peptides, the $\Delta^z$phe peptide can be either coupled to the resin support for synthesis of a formula I peptide or, alternatively can be incorporated into a previously synthesized peptide sequence to give compounds of formula II.

Alternatively, before the phe* peptide is incorporated with other subunits of the peptide sequence the $\Delta^E$ conformer maybe formed by photoisomerization and/or the amino nitrogen of phe* maybe alkylated.

Phe* peptide subunits may be joined to other subunits of the peptide sequence by either incorporating the phe* peptide directly onto a resin support for additional synthesis, or as a subunit later in the synthesis on a solid support. Alternatively, multiple amino acid subgroups may be coupled by the solution phase methodology or in combination with solid phase methodology.

The Phe* the alpha protecting group can be removed using any suitable procedure such as by using trifluoroacetic acid in methylene chloride, trifluoroacetic acid alone, or HCl in dioxane. The deprotection is carried out at a temperature of between 0° C. and room temperature. Other standard cleaving reagents and conditions for removal of specific α-amino protecting groups may be used. After removal of the α-amino protecting group the other amino protected amino acids are coupled step-wise in the desired order as previously set forth. Similarly the carboxy protecting group of the phe* subpeptide unit may be removed and incorporated to an appropriately deprotected subunit.

If the Phe* subunit is desired to be incorporated as part of the sequence, as in formula II peptide, the carboxy protecting group can be removed, and subsequently coupled to an existing sequence using a suitable coupling reagent.

After the desired amino acid sequence has been obtained, the peptide is removed from the resin. This can be done by hydrolysis such as by treatment of the resin bound polypeptide with an amino acid alcohol and acetic acid in dichloromethane (DCM). Protecting groups can also be removed by other procedures well known in the art. Typically protecting group removal is done after the peptide chain synthesis is complete but the protecting groups can be removed at any other appropriate time. Purification of peptides is principally accomplished through preparative reverse phase high performance liquid chromatography and those techniques known to those skilled in the art.

Synthesis of Protected Phe* Analogs ($R_1 = C_1-C_4$)

Compounds of this invention also include those Phe* derivatives that have $C_1-C_4$ modification of the alpha amino group.

Reaction Scheme II shows the making the compounds of formula 7A, wherein $R_4$ is methyl, ethyl, propyl, butyl, or like alkyl substituent of 1-4 carbon atoms of the alpha nitrogen of a given modified phenylalanine.

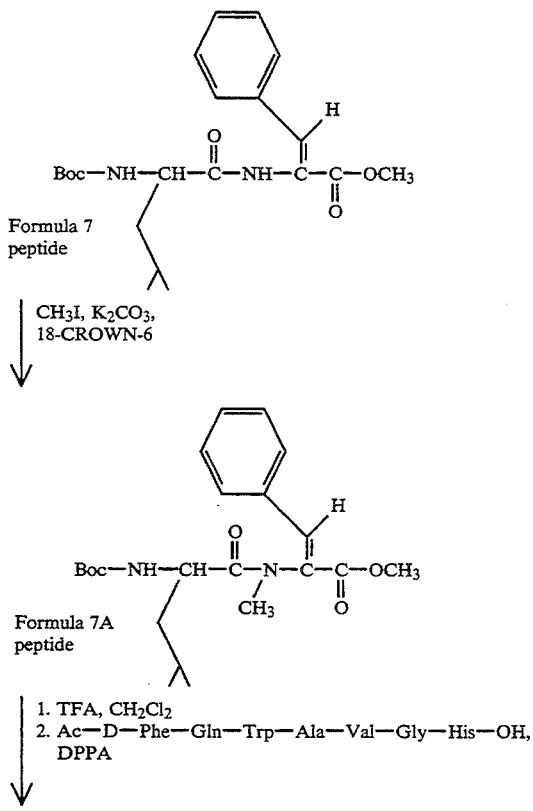

-continued
REACTION SCHEME II

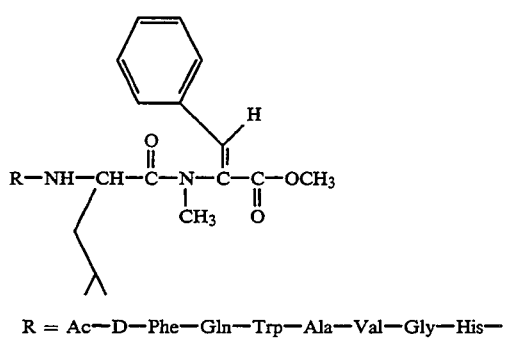

R = Ac—D—Phe—Gln—Trp—Ala—Val—Gly—His—

Alkylations can be performed by using suitable alkyl halides. Specifically, compounds of formula 7 wherein R is hydrogen can be subjected to a subsequent reaction with an alkyl halide to produce the modified dipeptide of formula 7A. Whown is reaction with methyl iodide, wherein the subsequent $R_4$ group is methyl. Other desired alkyated derivatives of C1–C4 may be formed using the corresponding alkylated halides.

According to Reaction scheme II a formula 7 peptide can be alkylated by reacting with a C1–C4 alkyl halide. Shown in reaction scheme II is Boc-Leu-$\Delta^z$-(CH$_3$)Phe-OMe synthesized by reacting Boc-Leu-$\Delta^z$-Phe-OMe with methyliodide in a solution of potassium carbonate in the presence of 18-crown-6. The methylated peptide Boc-Leu-$\Delta^z$-Phe-OMe is then reacted with the pentapeptide block Ac-D-Phe-Gln-Trp-Ala-Val-Gly-His-OH after deprotection of the Boc protecting group.

Alternatively one can perform reductive alkylation of a phe* peptide after its incorporation into a larger peptide sequence because of the selectivity of the alkylation reaction. Alkylation of the peptide may suitably be employed to synthesize those analogs of formula II having $R_1$ as a $C_1$–$C_4$ alkyl.

Photoisomerization of a 7 or 7A peptide is shown in reaction scheme III.

REACTION SCHEME III

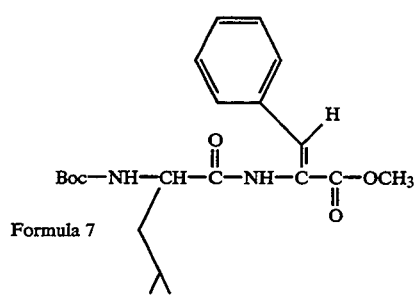

Formula 7

1. TFA, CH$_2$Cl$_2$
2. Ac—D—Phe—Gln—Trp—Ala—Val—Gly—His—OH, DPPA

-continued
REACTION SCHEME III

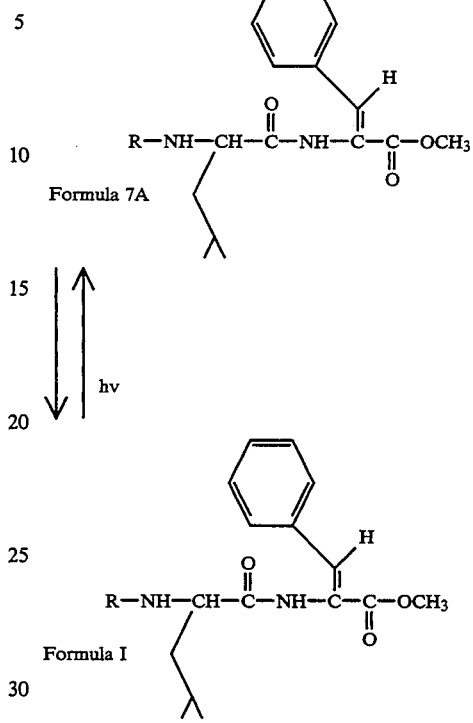

Specifically shown is Boc-Leu-$\Delta^z$-Phe-OMe photoisomerized to a isomeric mixture of the $\Delta^z$ and $\Delta^E$ configuration. Photoisomerization is done by placing the 7 or 7A peptide in a favorable light transducing solvent. A preferred solvent is DMF/MeOH. The peptide solution is then irradiated in a photolysis reaction chamber with suitable filtering. A light power source with a Mercury arc lamp is used to irradiated the sample. The reaction was sampled at different intervals to determine the ideal time and strength of irradiation by monitoring the reaction by analytical RP/HPLC. Each isomer is able to be isolated by preparative RP/HPLC and their structures confirmed analytically.

THERAPEUTIC USE

The ability of the peptide derivatives of this invention to act as agonists or antagonist of Bombesin can be demonstrated by the ability of such peptides to compete with radioiodinated bombesin/GRP for mammalian bombesin/GRP receptors using the method of Fanger, et al., Reg. Pept. 32: 241-251, 1991, and by the ability of such compounds to stimulate bombesin induced phosphatidylinositol turnover using the method of Fanget, et al., Rep. Pept 32: 241-251, 1991. Because the subject compounds interact with the bombesin receptor, knowledge of their agonism or antagonism of receptor responses allows one to indicated potential modes of therapy as known in the art bombesin acting compounds.

Stimulation/Inhibition of Digestion

Specific pharmacological effects of bombesin analogs to stimulate digestion have been elicited by systemic injection. For example, intravenous injection of bombesin analogs is able to stimulate gastric acid secretion [reviewed in Walsh, J., Annu. Rev. Physiol. 50, 41-63, (1988)]. Both peripheral and central administration of bombesin peptides delays the gastric emptying while also stimulating gastrointestinal smooth muscles in vitro. It has also been demonstrated, for example, exogenous administration of bombesin induces the release of both gastrin and somatostatin in isolated vascularly perfused rat stomachs. Similarly guinea pig atrium longitudinal muscle strips directly stimulate the frequency of spontaneous contractions and direct the contraction of the muscularis mucosase of the colon. However, it is to be noted that these effects may not occur if their administration is to the brain or spinal cord. The applicants use of the peptide to stimulate digestion are, therefore, useful when those effects are consistent with the necessary mechanisms of digestion and are consistent with peripheral administration (i.e., not being injected into the brain or spinal cord).

The natural history of peptic ulcer disease is one of recurrent exacerbations and remissions. As a result, ulcerative diseases should be treated as a chronic disorder. Peptic (esophageal, gastric, and duodenal) ulcers occur in areas of the gastrointestinal tract exposed to acid and pepsin. The compounds of the present invention which are antagonists of the bombesin receptor may be useful in the treatment of gastrointestinal and/or pancreatic ulcers and may be effective in resultant hypersecretions occurring from the pancreas and/or stomach, particularly hydrochloric acid and pepsin. As such, compounds of this invention may serve as an appropriate intervention to treat ulcers.

Stimulation/Inhibition of Growth

Binding of Bombesin to its cell surface receptor elicits cell mitogenic responses in a number of tissues. The initial demonstration that the bombesin peptides could function as mitogens was demonstrated on Swiss 3T3 murine embryonal fibroblasts [Rozengurt and Sinnett-Smith, BBRC 140, 379–385 (1983)]. Later studies by Represa [Represa J. J., et. al. Development 102, 87–96 (1988)] showed that bombesin could reactivate cell division and development in growth-arrested ocular vesicles. Similar increases in the clonal growth rate and colony-forming efficiency were observed by Willey et. al. 1984 for GRP and GRP analogs [Willey, J. C., et al., Exp. Cell Res.. 153, 245-248 (1984)]. A number of groups have observed the presence of high-affinity receptors for bombesin/GRP in a number of human small cell lung carcinomal cell lines and showed bombesin could elevate levels of thymidine incorporation with peptides added to the media [See Weber et al., J. Clin. Invest 75, 306–309 (1985); Carney, et al., Cancer Res. 47, 821–825, (1987)]. A measurable effect on gastrin cells in the antral mucosa of the rat stomach were noted by Lehy [Lehy et. al., Gastroenterology, 84, 914–919 (1983)] following the administration of bombesin. Chronic treatment with bombesin has also been shown to induce a dose-dependent pancreatic cell hypertrophy (Lhoste et al. 1985a). The applicants use of the peptide to stimulate growth, are therefore, useful when those effects are consistent with the necessary mechanisms of growth and are consistent with the effects seen with peripheral. administration.

Use of bombesin antagonist in cancer therapy is indicated for the treatment of small cell lung carcinomas (SCLC) and prostatic carcinomas and prevention of a variety of other cancer conditions. Those experienced in this field are readily aware of the circumstances requiring cancer therapy.

As used herein, the term "tumor tissue" means both benign and malignant tumors or neoplasms and includes melanomas, lymphomas. leukemias, and sarcomas. Illustrative examples of tumor tissues are: cutaneous such as malignant melanomas and mycosis fungoides; hematologic tumors such as leukemias, for example, acute lymphoblastic, acute myelocytic, or chronic myelocytic leukemia; lymphomas such as Hodgkin's disease or malignant lymphoma; gynecologic tumors such as ovarian and uterine tumors; urologic tumors such as those of the prostate, bladder, or testis; soft tissue sarcomas, osseus, or non-osseous sarcomas, and breast tumors; tumors of the pituitary, thyroid, and adrenal cortex; gastrointestinal tumors such as those of the esophagus, stomach, intestine, and colon; pancreatic and hepatic tumors; laryngeae papillomestasas; and lung tumors.

The term "controlling the growth" and the concept of treating a cancer means slowing, interrupting, arresting, or stopping the growth and metastases of a rapidly proliferating tumor in a warm blooded animal; it being understood that treatment in a warm blooded animal does not generally provide a "cure" for the tumor in the sense that necessarily the tumor tissue is destroyed or totally eliminated.

Therapeutic Administration

The appropriate dose of a peptide derivative of this invention when used in the treatment of-patient in need thereof is from 0.2 mg/kg to 250 mg/kg of patient body weight per day depending on other factors involving the particular patient and the peptide derivative selected. The suitable dose for a particular patient can be readily determined. Preferably from 1 to 4 daily doses would be administered typically with from 5 mg to 100 mg of active compound per dose. The amount of a peptide of this invention required can be readily determined by those skilled in the art.

The term "patient" used herein is taken to mean mammals such as primates, including humans, sheep, horses, cattle, pigs, dogs, cats, rats, and mice.

Although some of the peptide derivatives may survive passage through the gut following oral administration, applicants prefer non-oral administration, for example, subcutaneous, intravenous, intramuscular, or intraperitoneal; administration by depot injection; by implant preparation; or by application to the mucous membranes, such as, that of the nose, throat, and bronchial tubes, for example, in an aerosol can contain a peptide derivative of this invention in a spray or dry powder form.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable, or synthetic origin, for example, peanut oil, soybean oil, and mineral oil. In general, water, saline, aqueous dextrose and related sugar solutions, ethanol, and glycols such as propylene glycol or polyethylene glycol are preferred liquid carriers, particularly for injectable solutions.

EXAMPLES

This invention is illustrated by the following nonlimiting examples.

Example 1 p-toluenesulfonate D,L-3-phenylserine ethyl ester (1).

An ethanol solution (50 ml) of p-toluenesulfonic acid (0.067 mol, 12.7g) and D,L-3-phenylserine (Aldrich)(6.0 g, 0.033 mol) was refluxed for 24 h. The solvent was removed and the resulting residue repeatedly washed with ether yielding a white solid (12.8 g, yield 95%) $R_f(A)$ 0.63; m.p. 165°–167°.

tert-Butyloxycarbonyl-leucyl D,L-phenylserine (2).

A solution of Boc-leucine (1.7 g, 7.5 mol) in 30 ml of dry tetrahydrofuran was cooled to $-5°$ C. and N-methylmorpholine (0.99 g, 8.9 mol) and isobutyl chloroformate (1.0 g, 7.5 mol) were added and stirred for 1 h. A solution of 1 (3.0 g, 7.5 mol) in 10 ml of dioxane/water (7:3) containing triethylamine-(0.909 g, 8.9 mol) was prepared. The mixture was stirred for 3 h, water added and the tetrahydrofuran evaporated. The resulting oil was extracted with EtOAc and subjected to a normal workup yielding an oil (2.9 g, 0.007 mol, yield 94%) judged to be homogeneous on TLC ($R_f(A)$ 0.91, Rf(B) 0.70). The ester was dissolved in 20 ml of methanol and 20 ml of 1N sodium hydroxide added. The mixture was stirred for 3h then concentrated in vacuo. The aqueous solution was acidified with 4N hydrochloric acid while stirring on ice and the solution extracted with EtOAc. The pooled extracts were washed with saturated sodium chloride, dried over sodium sulfate and evaporated in vacuo to yield a white solid which was recrystallized from EtOAc/hexane (2.7g, 95% yield), $R_f(A)$ 0.79, $R_f(B)$ 0.83, m.p. 75°–78°.

Azlactone of Boc-Leu-$\Delta^z$Phe (3).

A solution of 2 (2.3 g, 6 mol) and sodium acetate (0.5 g) in 6 ml of acetic anhydride was stirred at room temperature for 8 h. The reaction was evaporated to dryness in vacuo. The resulting residue was stirred with EtOAc (60 ml) and water (20 ml), and the water layer separated from the EtOAc. The EtOAc extract was subjected to a normal workup and the resulting white solid recrystallized from ether/hexane, (yield 1.86 g, 90%); $R_f(A)$ 0.88, $R_f(B)$ 0.66; m.p. 118°–120° C.;

Boc-Leu-$\Delta^z$Phe-OMe (4).

Ring opening of Boc-Leu-$\Delta^z$-Phe-Azlactone was accomplished by placing 0.7105g (1.9 moles) of the peptide and 0.023g (.19 moles) of DMAP in 30–40 ml of methanol for approximately 12 hours. The reaction was worked up in ethyl acetate with acid and base washes to yield a white solid. The residue was recrystallized from ethyl acetate hexane (yield 0.70g); $R_f$ (EtOAc:Hexane 1:1) 0.48, $R_f$(EtoAc:Hexane:Acetone, 2:1:1) 0.77, $R_f$(t-BuOH:Hc. Ac:H20, 2:1:1) 0.89, m.p. 182° C. (uncorrected Gallenkamp).

Ac-D-Phe-Gln-Trp-Ala-Val-Gly-His-Leu-$\Delta^z$Phe-OMe (5).

T-Boc-Leu-$\Delta^z$Phe- was mixed in 30 ml $CH_2Cl_2$; TFA (1:0.75; v/v). The solvent was removed to give H-Leu-$\Delta^z$Phe-Ome. This residue was triturated from ether and isolated as a white solid. This was then reacted with Ac-D-Phe-Gln-Trp-Ala-Val-Gly-His-OH (36 mg) in 20 ml. DMF, adjusting the pH to 7.0 with diisopropylethylamine (DIEA) and adding diphenylphosphorylazide (DPPA;9 microliters). The deprotected Compound 4 was added to the reaction mixture at 0° C. and allowed to react overnight. The reaction mixture was then evaporated of DMF and the resulting mixture purified on Reverse Phase High Performance Liquid Chromatography (RP-HPLC). FAB-MS confirmed the desired mass of the product. Amino acid analysis was used to confirm the amino acid composition of the product was as expected.

Ac-D-Phe-Gln-Trp-Ala-Val-Gly-His-Leu-$\Delta^E$Phe-OMe (6).

The incorporation of dehydro-z-phenylalanine was accomplished through preparation of T-Boc-Leu-$\Delta^z$Phe-OMe via the Bergmann method. Sequence elongation to give the desired analog was accomplished with solution phase fragment coupling. Photoisomerization to the $\Delta^E$ was accomplished with Ac-D-Phe-Gln-Trp-Ala-Val-Gly-His-Leu-$\Delta^z$Phe-OMe. The $\Delta^z$ compound (10.0 mg) was dissolved in 300 ml DMF/MeOH (1:1, v/v) and irradiated in a photolysis reaction chamber (Ace Glass). A Hanovia power source was employed with a Mercury arc lamp adapted with a pyrex glass sleeve filter to filter uv light below 300 nm. The reaction chamber was water-cooled while stirring. The reaction was sampled at 3.5 and 5 hours while monitoring by analytical RP/HPLC. The reaction solution was then concentrated by rotary evaporation and purified by preparative RP/HPLC. The lyophilizate fractions were then analyzed by FAB/Ms and amino acid analysis confirming desired compounds.

Other examples synthesized by these type of procedures include:

(Ac-D-Phe$^1$, Leu8,$\Delta^z$Phe$^9$)litarin-OMe
(Ac-D-Phe$^1$, Leu$^8$, N(Me)$\Delta^Z$Phe$^9$)litorin-OMe
(Ac-D-Phe$^1$, Leu$^8$,N(Et)$\Delta^Z$Phe$^9$)litorin-OMe
(Ac-D-Phe$^1$, Leu$^8$, $\Delta^E$Phe$^9$)litorin-OMe
(Ac-D-Phe$^1$, D-Ala$^6$, Leu$^8$, N(Me) $\Delta^Z$Phe$^9$)litorin-OMe Compounds that could be made by these procedures include:

Glp-Gln-Trp-Ala-Val-Gly-$\Delta^z$Phe-Phe-Leu-OH.
Glp-Gln-Trp-Ala-Val-Gly-His-Leu-$\Delta^z$Phe-OMe.
Glp-Gln-Trp-Ala-Val-Gly-His-Leu-N(CH$_3$)$\Delta^z$Phe-OMe.
N$\alpha$-acetyl-D-phe-Gln-Trp-Ala-Val-His-$\Delta^E$Phe.
N$\alpha$-acetyl-$\Delta^z$Phe-Gly-Gln-Trp-Ala-Val-Gly-His-Leu.

Example 2

BINDING TO THE BOMBESIN RECEPTOR AS DEMONSTRATED BY IODINATED GRP

The pancreas from one or more mice were pooled and homogenized in 50 mM HEPES (pH 7.4) containing 120 mM NaCl, 5 mM KCl, and protease inhibitors (1 $\mu$g/ml aprotinin, leupeptin, pepstatin; 4 $\mu$g/ml bacitracin, antipain, bestatin; 100 $\mu$M PMSF; 1 mM EDTA) at 4° C. and centrifuged at 37,500 $\times$ g for 15 minutes. The pellet was resuspended in 50 mM HEPES (pH 7.4) containing 10 mM EDTA, 300 mM KCl, and protease inhibitors, and then incubated for 30 minutes at 4° C. The suspension was centrifuged as above and the pellet was washed two times in 50 mM HEPES (pH 7.4) containing 0.8 $\mu$g/ml thiorphan and protease inhibitors, and again centrifuged. The tissue was then resuspended in incubation buffer (1 ml per 4 mg pancreas) and incubated for 15 minutes at room temperature, then 250 $\mu$l were added to each assay tube to commence the assay. The assay tubes contained incubation buffer consisting of 50 mM HEPES (pH 7.4), 0.5% BSA, protease inhibitors, 2 mM MnCl$_2$, 0.8 $\mu$g/ml thiorphan, 1 $\mu$M somatostatin, and concentrations of $^{125}$I-GRP and peptides as needed in a final volume of 500 μl. The assay was allowed to proceed to equilibrium for 90 minutes at room temperature. After this time, the contents of each tube were rapidly filtered over Whatman GF/B filters presoaked in 0.1% polyethyleneimine and the tubes and filters were rapidly washed three times with ice-cold 50 mM HEPES (pH 7.4). Filter-bound radioactivity was quantitated in a gamma counter. Competition of iodinated GRP binding by test compounds or standards was expressed as a percentage of $^{125}$I-GRP binding in the absence of peptide. Affinity and maximal binding were calculated with LIGAND (Biosoft, Cambridge, UK).

Example 3

EFFECT OF ANALOGS ON THE BOMBESIN RECEPTOR AS DEMONSTRATED BY PHOSPHATIDYLINOSITOL TURNOVER

Pancrea from mice were chopped at 350 μm with a tissue chopper and pooled in Krebs-Hepes buffer [118 mM NaCl, 1.2 mM $K_2PO_4$, 4.7 mM KCl, 1.2 mM $MgSO_4$, 1.0 mM $CaCl_2$, 11.7 mM glucose, 20 mM Hepes (pH 7.4)]. The chopped tissue was washed once with oxygenated Krebs-Hepes, then incubated for 30 minutes in 37° C. oxygenated Krebs-Hepes buffer with fresh buffer after 15 minutes. The tissue was then incubated in this buffer containing 200 μCi of [$^3$H]inositot at 37° C. for 1 hour. The tissue was then washed twice and incubated for another 30 minutes in oxygenated Krebs-Hepes (containing 10 mM Li+) at 37° C. and with fresh buffer change after 15 minutes. Portions of the tissue mass (approximately 10 mg per assay tube) were then placed in Li+ buffer with protease inhibitors (40 μg/ml bacitracin, 4 μg/ml leupeptin, 4 μg/ml chymostatin, 0.8 μg/ml thiorphan), 0.1% BSA, and 0.1-1000 μM peptide. After 60 minutes at room temperature, the phosphatidylinositol turnover was terminated by the addition of 940 μl chloroform:methanol (1:2), followed by 310 μl chloroform, followed by 310 μl water. Each tube was then vortexed three times for 5 seconds each time and then centrifuged at 25C0 × g for 8 minutes to separate the phases. 50 μl of the bottom phase (chloroform) was withdrawn from each tube and placed in a counting vial, dried, and counted in scintillation fluid. 900 μl of the top (aqueous) phase was then mixed with 2.1 ml water and loaded onto a 0.5 ml Biorad AG-1×8 (formate) ion exchange column. The material on the columns was washed in order with: 1) 10 ml of water 2) 5 ml of B mM disodium tetraborate/60 mM sodium formate 3) 10 ml of 1M ammonium formate in 0.1M formic acid. The final (third) wash was collected and one ml was mixed with 14 ml of Bio-Safe or E-Colume scintillant and counted. The ratio of these counts (total inositol phosphates) to the corresponding organic phase counts (inositol incorporated into the tissue) was then calculated for each sample. The ratios in the presence of test compound and/or standards were then compared to the ratios for control tubes (i.e., no stimulating agonist). The abilities of test compounds to stimulate phosphatidylinositol turnover were determined with the aid of a computer program.

Listed below in Table 1 are results of the some experiments for receptor affinity (Kd) and PI turnover for the bombesin analogs synthesized.

TABLE 1

| Dissociation Constants and Efficacy of Dehydrophenylalanine-containing Litorin Analogs | |
|---|---|
| Analog | Kd (nM) Agonist Antagonist |
| I Gastin Releasing Peptide | 0.07 + − |
| II Bombesin | 0.15 + − |
| III Litorin | 0.075 + − |
| IV (Ac-D-Phe$^1$,Leu$^8$,Δ$^Z$Phe9)litorin-OMe | 1.18 (+) + |
| V (Ac-D-Phe$^1$,Leu$^8$,N(Me)Δ$^Z$Phe$^9$)litorin-OMe | (+) N.D. N.D. |
| VI (Ac-D-Phe$^1$,Leu$^8$,N(Et)Δ$^Z$Phe9)litorin-OMe | (+) N.D. N.D |
| VII (Ac-D-Phe$^1$,Leu$^8$,Δ$^E$Phe$^9$)litorin-OMe | 18.56 (+) (−) |
| VIII (Ac-D-Phe$^1$,D-Ala$^6$,Leu$^8$,N(Me)Δ$^Z$Phe$^9$)litorin-OMe | 65.33 + − |
| IX (Phe$^8$Ψ[CH$_2$SO$_2$]Leu$^9$litorin | 9.9 (−) 30 |

Positive and negative agonist or antagonist activity indicated by a + or − sign respectively. Plus and minus signs with parenthesis indicate preliminary results from testing.

Table 1 The peptides listed were tested in both a competitive binding and PI-turnover assay in mouse pancreas as described in Methods. Analog IV binds with highest affinity. IV is an antagonist, but as seen in FIG. 2 has partial agonist activity. The Δ$^E$ conformer is an agonist with weaker receptor affinity than the Δ$^z$. N-alkylation of the Δ$^Z$Phe residue appears to yield an agonist (VIII). These are contrasted with a previously reported pseudopeptide antagonist (IX) containing a backbone substitution at the penultimate amide bond.

What is claimed is:

1. Claimed are peptides of the formula 1:

Glp-Gln-Trp-Ala-Val-Gly-$A_1$-Phe*-$A_2$-Y (formula 1)

wherein;

$A_1$ is His, Leu, His-Leu, or a bond;

Phe* is a modified phenylalanine derivative selected from the group consisting of $\Delta^z$Phe, and $\Delta^E$Phe wherein said derivatives $\Delta^z$Phe are further substituted by a $C_1$–$C_4$ alkyl group at the alpha nitrogen;

$A_2$ is Phe, Leu, Phe-Leu, or a bond; and

Y is a carboxy terminal substituent selected from OH, ($C_1$–$C_8$) alkoxyester, carboxamide, mono or di ($C_1$–$C_8$) alkyl amide, mono or di ($C_1$–$C_8$) alkylamine, ($C_1$–$C_4$) thioalkylether; or said compounds of formula 1 are pharmaceutically acceptable salt thereof.

2. Claimed are peptides of the formula 1;

Glp-Gln-Trp-Ala-Val-Gly-$A_1$-Phe*-$A_2$-Y (formula 1)

wherein;

$A_1$ is His, Leu, His-Leu, or a bond;

Phe* is a modified phenylalanine derivative selected from the group consisting of $\Delta^z$Phe;

$A_2$ is Phe, Leu, Phe-Leu, or a bond; and

Y is a carboxy terminal substituent selected from OH, ($C_1$–$C_8$) alkoxyester, carboxamide, mono or di ($C_1$–$C_8$) alkyl amide, mono or di ($C_1$–$C_8$) alkylamine, ($C_1$–$C_4$) thioalkylether; or said compounds of formula 1 are pharmaceutically acceptable salt thereof.

3. A method of treating ulcers in a patient in need thereof which comprises administering to the patient an effective amount of a peptide of claim 2.

4. A method of inhibiting cancerous cell growth in organ tissues, wherein said organ tissues are selected from lung and pancreatic, in a patient in need thereof which comprises administering to the patient an effective amount of a peptide derivative of claim 2.

5. A compound of the formula Ac-phe-Gln-Trp-Ala-Val-Gly-His-Leu-N(Me)$\Delta^z$Phe-OMe.

6. A compound of the formula Ac-phe-Gln-Trp-Ala-Val-Gly-His-Leu-N(Et)$\Delta^z$Phe-OMe.

7. A compound of the formula Ac-phe-Gln-Trp-Ala-Val-Gly-His-Leu-$\Delta^E$Phe-OMe.

8. A peptide as in claims 1, 2, 5, 6 or 7, which may be a pharmaceutically acceptable salt thereof or a pharmaceutical composition which utilizes a pharmaceutically acceptable carrier.

* * * * *